United States Patent [19]

Hamano et al.

[11] Patent Number: 5,902,627
[45] Date of Patent: *May 11, 1999

[54] PROCESS FOR THE PRODUCTION OF ALKALI-TREATED YOGURT POWDER POSSESSING AN IMMUNOLOGICAL ACTIVITY

[75] Inventors: Atushi Hamano, Inashiki-gun; Masahide Tani, Tsukuba; Takashi Sasaki, Sakura; Tomohiro Kurokawa, Takasaki; Hiroshi Tanabe, Kamihikuoka; Mayumi Makiyama, Maebashi, all of Japan

[73] Assignees: National Federation of Agricultural Co-Operative Associations; Scientific Feed Laboratory Co., Ltd., both of Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/959,742

[22] Filed: Oct. 28, 1997

Related U.S. Application Data

[63] Continuation of application No. 08/503,215, Jul. 17, 1995, abandoned.

[30] Foreign Application Priority Data

Sep. 26, 1994 [JP] Japan .................................. 6-256251

[51] Int. Cl.⁶ .................................................. A23C 17/00
[52] U.S. Cl. .............................. 426/583; 426/34; 426/61; 426/580
[58] Field of Search .................................. 426/583, 2, 34, 426/42, 43, 61, 384, 385, 443, 465, 519, 520, 580

[56] References Cited

U.S. PATENT DOCUMENTS

| | | | |
|---|---|---|---|
| 2,095,767 | 10/1937 | Shaw | 426/583 |
| 2,465,875 | 3/1949 | Hopkins | 426/583 |
| 4,289,788 | 9/1981 | Cajigas | 426/583 |
| 5,290,571 | 3/1994 | Bounous et al. | 426/72 X |
| 5,474,932 | 12/1995 | Bengmark et al. | 435/252.9 |

FOREIGN PATENT DOCUMENTS

| | | |
|---|---|---|
| 0063438 | 10/1982 | European Pat. Off. . |
| 0303477 | 2/1989 | European Pat. Off. . |
| 0303946 | 2/1989 | European Pat. Off. . |
| 1005116 | 4/1952 | France . |
| 151289 | 12/1931 | Germany . |
| 1692456 | 8/1971 | Germany . |

OTHER PUBLICATIONS

Anon., 8(11):P1684 FSTA, abstracting Confectionery Manufacture and Marketing (1983) 20(5) 12.

Halpern, G.M., et al., Influence of Long–Term Yoghurt Consumption in Young Adults, Int. J. Immunotherapy VII (4) (1991), pp. 205–210.

Chemisches Zentralblatt, No. 42, 1960, p. 14214 & Prumysl Potravin, vol. 8, 1957, pp. 292–290, Josef Sulc et al.

Derwent Publications Ltd., London, GB; AN 70–94674R & JP–B–45 040 259 (Toyo Brewing Co., Ltd.) 1970, abstract.

Patent Abstracts of Japan, vol. 16, N. 176 (C–0934), Apr. 27, 1992 & JP–A–04–020263 (Tomoji Tanaka), Jan. 23, 1992.

*Primary Examiner*—Leslie Wong
*Attorney, Agent, or Firm*—Evenson, McKeown, Edwards & Lenahan, P.L.L.C.

[57] ABSTRACT

A process for the production of yogurt powder possessing an immunological activity, in which yogurt is heated at 60° to 100° C. and it is provided with an alkaline agent to adjust the yogurt to pH 7.0 to 96, and thereafter dried to a powder. Before powdering, the yogurt may be subjected either to the addition of a non-ionic surfactant or to high pressure homogenizing treatment. Yogurt retaining immunological activity can be used effectively as food and feed.

6 Claims, 1 Drawing Sheet

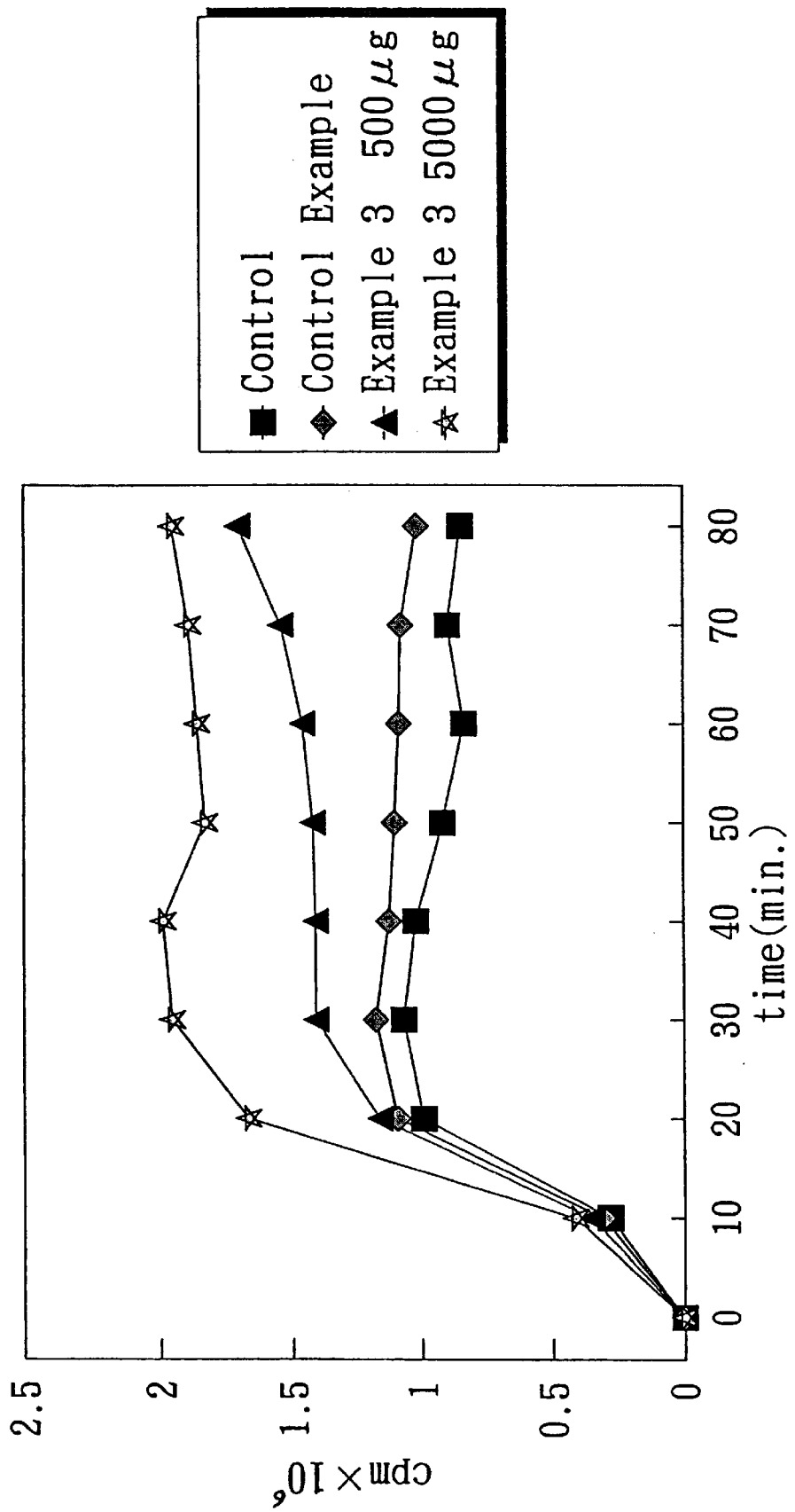
Figure.1 Phagocytosis of Neutropohiles

PROCESS FOR THE PRODUCTION OF ALKALI-TREATED YOGURT POWDER POSSESSING AN IMMUNOLOGICAL ACTIVITY

This application is a continuation of application Ser. No. 08/503,215, filed on Jul. 17, 1995, now abandoned.

FIELD OF THE INVENTION

This invention relates to a process for the production of yogurt powder possessing an immunological activity, and more particularly to a process for the production of yogurt powder containing an immunological activator derived from the destroyed lactic acid bacteria in the heated yogurt and having a lower adhesion and hygroscopicity. The yogurt powder thus prepared according to the present invention is used as food and feed.

DESCRIPTION OF THE PRIOR ART

Conventionally, since yogurt as food had a short preservation period from production date to expiration date, any yogurt past its expiration date was wasted. Since diversification of customers' needs forced manufacturers to produce many varieties of products, a lot of product loss occurred at the time of the change of manufacturing products. The resulting merchandise loss and expenses for waste described above were serious disadvantages from the point of view of manufacturing cost. In addition, conventional yogurt has other weak points, such as degradation of value and function of food due to autolysis of lactic acid bacteria in the yogurt when kept raw for a long time.

The only other way to use the wasted yogurt other than as a food was as a milk substitute to animals by drying it with bran, in a drum dryer and the like.

The waste raw yogurt is useful for a milk substitute in liquid feed, however it is not so useful to add to dry feeds, because feeding boxes are messed up and the entire feed deteriorated by microbial contamination When it is dried by dryers, such as a drum dryer, the product was dried into an agglomeration rather than powder. Its high adhesion and hygroscopicity prevented mixing the product with usual powder feed. Therefore, there was no other way except directly.

Further, immunological activity derived from lactic acid bacteria in the yogurt could not be used efficiently.

Up to this time, the objects of feeding yogurt is only to increase palatability for animals and to use it as a nutritious resource. Yogurt powder containing immunological activity derived from the lactic acid bacteria has not been used as a high value-added feed, much less as food and the like.

Accordingly, it is an object of the present invention to provide a yogurt powder which can be used as a feed additive by mixing with feed.

It is another object of the present invention to provide a process for the production of yogurt powder which carries a high immunological activity derived from the lactic acid bacteria in the heated yogurt that is usable for food and the like.

SUMMARY OF THE INVENTION

The inventors of this invention have found that yogurt powder can be produced, when yogurt is heated and treated with an alkaline agent to solubilize a casein portion of the protein therein in water. Thereafter, the yogurt is subjected to the addition of a surfactant or to high pressure treatment by use of a high pressure homogenizer or to addition of a drying carrier, solely or in combination, for drying the yogurt by a spray drying method or the like.

The yogurt powder prepared according to the present invention retains an immunological activity derived from the lactic acid bacteria and the like.

The resulting yogurt powder can be used as a feed additive having an immunological activity or as an ingredient for health food. The process of this invention can be modified in accordance with usage and purposes.

The yogurt used as a starting material in this invention usually includes any yogurt which may be of curd form and of liquid form; for example, yogurt produced for food and drink, product loss, returned yogurt of which tasting periods have expired.

An object of the heat treatment herein is that the yogurt is heated at more than 60° C. to sterilize it and to solubilize a casein portion of protein therein smoothly in water. The optimum temperature of the heat treatment is preferably 80 to 95° C.

The term "alkaline agent" herein includes sodium hydroxide, potassium hydroxide and the like. An object of this addition is that the pH of yogurt reach more than 7.0 to solubilize casein of the yogurt in water, and also that the cells' surfaces are treated with it to stabilize the immunological activity of the destroyed lactic acid bacteria in the heated yogurt. The optimum pH is preferably 8.3 to 9.6.

The term "surfactant" herein includes a non-ionic surfactant with HLB (hydrophile-lipophile balance) value of more than 7.0. An object of this use is that a surfactant is added in 0.1 to 10.0% to an amount of the yogurt to disperse fat smoothly, and also that the cells' surfaces are treated with it to stabilize the immunological activity of the destroyed lactic acid bacteria in the heated yogurt.

The surfactant to be used includes, for example, polyoxyethylene sorbitan fatty acid ester, sucrose fatty acid ester. Any of these with 9.0 to 15.0 in HLB is acceptable The optimum addition is preferably 0.3 to 5% to an amount of the yogurt.

The term "high pressure treatment" herein means pressurizing the yogurt momentarily in about 50 to 1000 kg/cm$^2$ by use of a high pressure homogenizer. An object of this use of high pressure treatment is that the cells' surfaces are destroyed so that cell walls consisting of sugar-lipid and sugar-protein can be easily removed.

The term "drying carrier" herein includes dextrin and lactose and the like. An object of this use is that a drying carrier is added in more than 2% to an amount of the yogurt to reduce adhesion and hygroscopicity at the moment of drying the yogurt. Preferably, the DE value (dextrose equivalent value) of dextrin is 7.0 to 12.0, and the optimum addition is in 5 to 20% to an amount of the yogurt.

Concerning the drying method herein, any well-known method, such as freeze drying, spray drying and vacuum drying may be used but the optimum method in terms of cost is spray drying.

The yogurt powder thus prepared according to the present invention not only may be mixed easily with feed, but it also possess a high immunological activity It can also be used for food and the like.

For example, when the resulting yogurt powder is administered to mice before inoculating a fatal amount of *E. coli* into mice, the administered mice survive, while all or most of the mice in a non-administered group die.

These animal tests prove the high immunological activity of the yogurt powder which can provide feed having an immunological activity and ingredients for a new type of food and the like.

BRIEF DESCRIPTION OF THE DRAWING

The invention will be best understood by reference to the following detailed description of an illustrated embodiment taken in consideration with the accompanying drawing, in which:

FIG. 1 is a graphic illustration of the results obtained in tests in which phagocytosis values of splenic cells of administered mice were found.

DETAILED DESCRIPTION OF THE INVENTION

This invention will be more clearly understood with reference to the following examples and control example.

CONTROL EXAMPLE

One hundred kilograms of yogurt (11% of solid contents) was thrown into a mixer equipped with a jacket to heat up the yogurt until it became 85° C. Thereafter, while stirring the yogurt, 10 kilograms of bran was thrown into the mixer to dry the product at 800° C. by use of a drum dryer. As a result, 16.8 kilograms of agglomerate substance was obtained.

EXAMPLE 1

One hundred kilograms of yogurt (11% of solid contents) was thrown into a mixer equipped with a jacket, and heated to 90° C. While stirring the yogurt, 40% solution of sodium hydroxide was added to adjust the yogurt to around pH 9.0. 10 kilograms of dextrin was also thrown into the mixer. Furthermore, the mixture was filtered through a sieve with 60 mesh after being mixed well. Finally, the filtrate was dried on a spray dryer under inlet temperatures of 170° C. and outlet temperatures of 85° C. As a result, 18.5 kilograms of dried yogurt powder was obtained.

EXAMPLE 2

One hundred kilograms of yogurt (11% of solid contents) was thrown into a mixer equipped with a jacket to heat the yogurt to 90° C. While stirring the yogurt, 40% solution of sodium hydroxide was added to adjust the yogurt to around pH 9.0. Successively, 0.5% of sucrose fatty acid ester was added to an amount of the yogurt, and also 10 kilograms of dextrin was thrown into the mixer. Furthermore, the mixture was filtered through a sieve with 60 mesh after being mixed well. Finally, the filtrate was dried on a spray dryer under inlet temperatures of 170° C. and outlet temperatures of 85° C. As a result, 18.5 kilograms of dried yogurt powder was obtained.

EXAMPLE 3

One hundred kilograms of yogurt (11% of solid contents) was thrown into a mixer equipped with a jacket to heat the yogurt to 90° C. While stirring the yogurt, 40% solution of sodium hydroxide was added to adjust the yogurt to around pH 9.0. Successively, 0.5% of sucrose fatty acid ester was added to an amount of the yogurt, and 10 kilograms of dextrin was also thrown into the mixer. Furthermore, the mixture was filtered through a sieve with 60 mesh after being mixed well. Finally, the filtrate was subjected to 100 kg/cm$^2$ of pressure treatment through a high pressure homogenizer to dry it on a spray dryer under inlet temperatures of 170° C. and outlet temperatures of 85° C. As a result, 18.5 kilograms of dried yogurt powder was obtained.

In order to investigate the fluidity and hygroscopicity of the dry matters obtained in the above control and test examples, the following two points were measured: (1) angle of repose and (2) successive loss on drying at room temperature Table 1 shows the results. From this it was found that the yogurt powder herein possessed high fluidity and low hygroscopicity, and that its physical properties were improved in comparison with the control example.

TABLE 1

|  | Angle of Repose | Loss on Drying (%) | | |
| --- | --- | --- | --- | --- |
|  |  | 0 day | 1st day | 2nd day |
| Example 1 | 42° | 4.71 | 4.88 | 4.99 |
| Example 2 | 41° | 4.65 | 4.86 | 4.98 |
| Example 3 | 36° | 4.65 | 4.72 | 4.98 |
| Control Example | >50° | 7.31 | 11.68 | 12.66 |

Experiment 1

In order to observe the life or death of mice inoculated with *E. coli,* the yogurt powder obtained in the above control and test examples was administered into the abdominal cavities of 10 mice in the amount of 5 mg/per mouser and thereafter dosages of *E. coli* in amounts fatal to mice was inoculated into the abdominal cavities of the mice. As a control, only *E. coli* was inoculated into mice of the same number.

Table 2 shows the results. From this, it was confirmed that the yogurt powder herein reinforced the infectious resistance of mice against *E. coli,* and that this powder possessed a sufficiently higher immunological activity in comparison with the control example.

TABLE 2

|  | No. Dead after Inoculation | | | Total # | Total # |
| --- | --- | --- | --- | --- | --- |
|  | 1st day | 2nd day | 3rd day | Dead | surviving |
| Example 1 | 2 | 1 | 0 | 3 | 7 |
| Example 2 | 2 | 0 | 0 | 2 | 8 |
| Example 3 | 0 | 0 | 0 | 0 | 10 |
| Control Exp. | 6 | 1 | 0 | 7 | 3 |
| Control | 7 | 3 | 0 | 10 | 0 |

| Phagocytosis of Neutrophiles | |
| --- | --- |
| Control | |
| Control Example | |
| Example 3 | 500 μg |
| Example 3 (min.) | 5000 μg |

Experiment 2

In order to measure the phagocytosis of neutrophiles in the spleens of mice by a chemiluminescence method on the basis of luminol reaction, the yogurt powder obtained in the above example was floated in physiological saline to administer the floating solution directly into the stomachs of mice with a tube, and the spleens of mice were removed on the third day after the administration to adjust cell sap to $4 \times 10^6$ cells/ml by 10 mM-HEPES added MEM.

As a result, the phagocytosis of splenic cells (neutrophiles) of the administered mice increased. Therefore, it was proved that the administration of the yogurt powder activated immunocomplement cells. FIG. 1 shows the results.

It should also be understood that the foregoing relates to only a preferred embodiment of the invention, and that it is intended to cover all changes and modifications of the example of the invention herein chosen for the purposes of disclosure, which do not constitute departures from the spirit and scope of the invention.

What is claimed is:

1. A process for producing yogurt powder for food and feed having an immunological activity, which comprises:

heating yogurt to a temperature within a range of from 60° C. to 100° C.;

adjusting pH of the heated yogurt to more than 7.0 with an alkaline agent to thereby stabilize immunological activity of the destroyed lactic acid bacteria; and drying resultant yogurt to powder.

2. A process for producing yogurt powder for food and feed having an immunological activity, as claimed in claim 1, wherein said pH of the heated yogurt is adjusted within a range of from 7.0 to 9.6.

3. A process for producing yogurt powder for food and feed having an immunological activity, as claimed in claim 1, wherein a surfactant is added to the heated and pH adjusted yogurt.

4. A process for producing yogurt powder or food and feed having an immunological activity, as claimed in claim 3, wherein HLB value of the surfactant is more than 7.0, and the surfactant is added to said yogurt in an amount of from 0.1 to 1.0%.

5. A process for producing yogurt powder for food and feed having an immunological activity, as claimed in claim 1, wherein said heated and pH adjusted yogurt is subjected to a high pressure treatment under 50 to 1000 kg/cm$^2$.

6. A process for producing yogurt powder for food and feed having an immunological activity, as claimed in claim 5, wherein means for said high pressure treatment comprises a high pressure homogenizer.

* * * * *